US010064623B2

(12) United States Patent
Soutorine et al.

(10) Patent No.: US 10,064,623 B2
(45) Date of Patent: Sep. 4, 2018

(54) SURGICAL CLIP AND CLIP MANIPULATION DEVICE THEREFOR

(75) Inventors: Mikhail Soutorine, Oakleigh (AU); Artem Nikolaevich Chernov-Haraev, Moscow (RU); Sergei Dimitrievich Prokoshin, Moscow (RU); Elena Prokopievna Ryklina, Moscow (RU); Irina Yurievna Khmelvskaya, Moscow (RU); Andrey Victorovich Korotitskiy, Moscow (RU); Rouslan Valereevich Ipatkin, Moscow (RU)

(73) Assignees: Globetek 2000 Pty Ltd, Brighton (AU); The Federal State Autonomous Educational Institution of the Higher Professional Education "National University of Science and Technology", Moscow (RU)

( * ) Notice: Subject to any disclaimer, the term of this patent is extended or adjusted under 35 U.S.C. 154(b) by 381 days.

(21) Appl. No.: 13/991,831

(22) PCT Filed: Dec. 7, 2011

(86) PCT No.: PCT/AU2011/001586
§ 371 (c)(1),
(2), (4) Date: Nov. 14, 2013

(87) PCT Pub. No.: WO2012/075532
PCT Pub. Date: Jun. 14, 2012

(65) Prior Publication Data
US 2014/0058411 A1     Feb. 27, 2014

(30) Foreign Application Priority Data
Dec. 7, 2010  (WO) ............... PCT/RU2010/00735

(51) Int. Cl.
*A61B 17/122*     (2006.01)
*A61B 17/08*      (2006.01)
(Continued)

(52) U.S. Cl.
CPC ............ *A61B 17/083* (2013.01); *A61B 17/10* (2013.01); *A61B 17/122* (2013.01);
(Continued)

(58) Field of Classification Search
CPC ..... A61B 17/083; A61B 17/10; A61B 17/105; A61B 17/1227; A61B 17/30; A61B 17/128; A61B 17/1285
(Continued)

(56) References Cited

U.S. PATENT DOCUMENTS 3,120,230 A * 2/1964 Skold ............... A61B 17/122
                                                123/634
3,867,944 A * 2/1975 Samuels ........... A61B 17/122
                                                24/23 W
(Continued)

FOREIGN PATENT DOCUMENTS

EP     1747761 A1   1/2007
FR     2756767      6/1998
(Continued)

OTHER PUBLICATIONS

PCT Written Opinion for International Application No. PCT/AU2011/001586, date of completion Apr. 5, 2012, 7 pages.
(Continued)

*Primary Examiner* — Kathleen Holwerda
(74) *Attorney, Agent, or Firm* — Brinks Gilson & Lione

(57) ABSTRACT

Some embodiments relate to a clip comprising: a base portion; first and second opposed arms coupled to the base portion; and first and second opposed jaws coupled to the respective first and second arms, the first and second
(Continued)

opposed jaws each having an inwardly extending portion that extends towards the base portion; wherein at least the base portion is formed of a shape memory alloy tending to force the first and second arms toward each other when a temperature of the base portion meets or exceeds a transformation temperature of the base portion.

21 Claims, 5 Drawing Sheets

(51) Int. Cl.
  *A61B 17/128* (2006.01)
  *A61B 17/10* (2006.01)
  *A61B 17/30* (2006.01)
  *A61B 17/00* (2006.01)

(52) U.S. Cl.
  CPC ........ *A61B 17/128* (2013.01); *A61B 17/1285* (2013.01); *A61B 17/30* (2013.01); *A61B 2017/00867* (2013.01)

(58) Field of Classification Search
  USPC ........ 606/139, 142, 143, 151, 157, 158, 219
  See application file for complete search history.

(56) References Cited

U.S. PATENT DOCUMENTS

| | | | | |
|---|---|---|---|---|
| 3,980,861 | A * | 9/1976 | Fukunaga | 219/230 |
| 4,485,816 | A * | 12/1984 | Krumme | A61B 17/0644 219/201 |
| 4,586,503 | A * | 5/1986 | Kirsch | A61B 17/083 606/151 |
| 4,805,618 | A * | 2/1989 | Ueda | A61F 6/206 128/831 |
| 4,834,096 | A * | 5/1989 | Oh | A61B 17/122 606/158 |
| 5,022,126 | A | 6/1991 | Davis | |
| 5,171,252 | A * | 12/1992 | Friedland | A61B 17/122 227/902 |
| 5,246,443 | A * | 9/1993 | Mai | 606/78 |
| 5,250,046 | A * | 10/1993 | Lee | 606/29 |
| 6,193,732 | B1 | 2/2001 | Frantzen et al. | |
| 6,348,064 | B1 * | 2/2002 | Kanner | 606/219 |
| 6,547,783 | B1 * | 4/2003 | Vilendrer et al. | 606/20 |
| 6,607,542 | B1 * | 8/2003 | Wild | 606/157 |
| 6,746,461 | B2 | 6/2004 | Fry | |
| 7,112,214 | B2 * | 9/2006 | Peterson | A61B 17/064 606/142 |
| 2002/0111641 | A1 | 8/2002 | Peterson et al. | |
| 2007/0088412 | A1 * | 4/2007 | Ashman et al. | 607/96 |
| 2007/0213747 | A1 * | 9/2007 | Monassevitch | A61B 17/0643 606/151 |
| 2011/0230900 | A1 * | 9/2011 | Sarradon | A61B 17/0644 606/151 |
| 2012/0059394 | A1 * | 3/2012 | Brenner | A61B 1/00087 606/142 |
| 2013/0079760 | A1 * | 3/2013 | Twomey et al. | 606/13 |

FOREIGN PATENT DOCUMENTS

| | | |
|---|---|---|
| JP | 56-23942 A | 3/1981 |
| JP | 61-143049 A | 6/1986 |
| JP | 63-288147 | 11/1988 |
| JP | 6-47048 | 2/1994 |
| JP | 2005-007151 A | 1/2005 |
| JP | 2005-505337 A | 2/2005 |
| JP | 2010-051810 A | 3/2010 |
| JP | 2010-507454 A | 3/2010 |
| JP | 2010-136749 A | 6/2010 |
| JP | 2010-207263 A | 9/2010 |
| RU | 2052979 C1 | 1/1996 |
| RU | 2213529 C2 | 10/2003 |
| RU | 2241391 C1 | 12/2004 |
| WO | WO 00/40159 | 7/2000 |
| WO | WO 2004/080314 A | 9/2004 |
| WO | WO 2008/0517464 A2 | 5/2008 |
| WO | WO 2010/055232 A1 | 5/2010 |

OTHER PUBLICATIONS

PCT International Search Report for International Application No. PCT/AU2011/001586, date of completion Apr. 5, 2012, 7 pages.
PCT International Preliminary Report on Patentability for International Application No. PCT/AU2011/001586, dated Jun. 12, 2013, 8 pages.
Office Action dated Oct. 19, 2017, Japanese application No. 2016-247381.
English Translation of Office Action dated Oct. 19, 2017, in Japanese application No. 2016-247381.

* cited by examiner

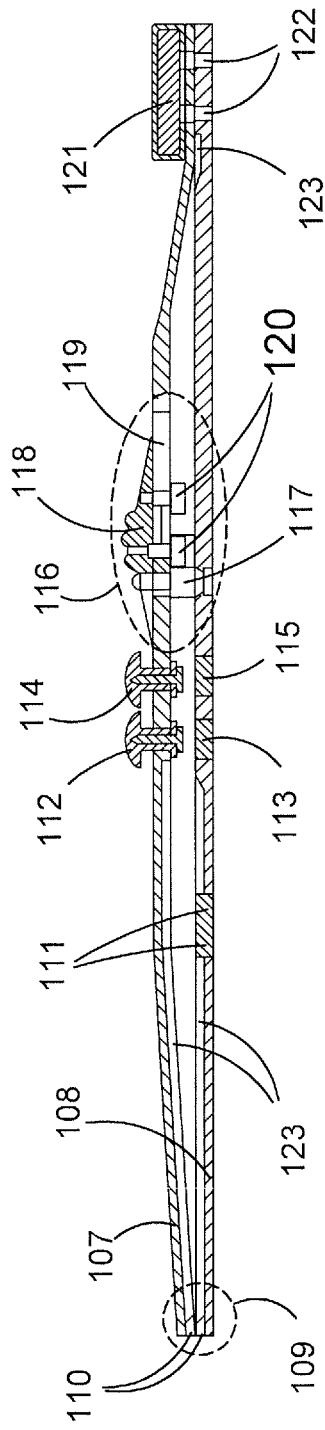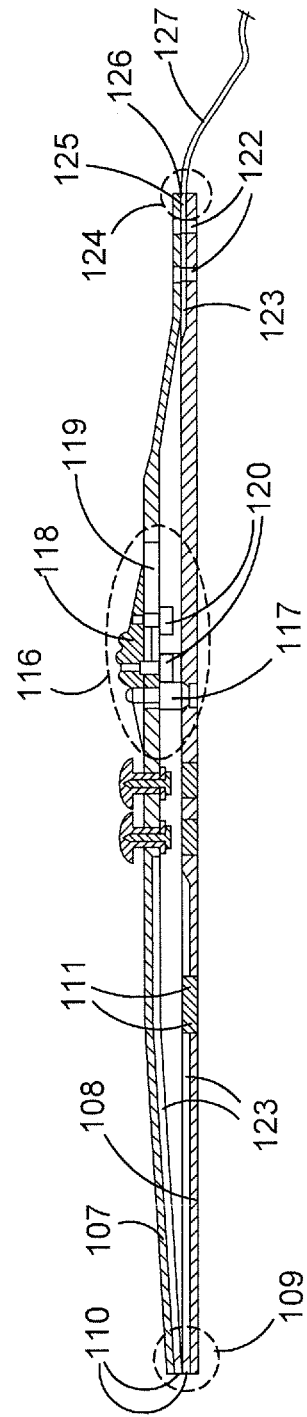

SURGICAL CLIP AND CLIP MANIPULATION DEVICE THEREFOR

CROSS-REFERENCE TO RELATED APPLICATIONS

This application is a National Stage application of PCT International Application No. PCT/AU2011/001586, filed 7 Dec. 2011, which claims priority to PCT International Application No. PCT/RU2010/000735, filed 7 Dec. 2010, the entire contents of which is hereby explicitly incorporated by reference as if it were written herein.

TECHNICAL FIELD

Described embodiments relate generally to metallic clips, such as surgical clips, and manipulation devices therefore. Such embodiments may be applied generally to open and endoscopic (laparoscopic) surgery. Embodiments can be used for such operations as cholecystectomy, appendectomy, gastrectomy, hemicolectomy, fund-application, cardiovascular and other operations which require tissue clipping or clamping in vessels.

BACKGROUND

In some situations, it is necessary to close off a tubular structure, for example in order to prevent further flow of a fluid through the structure. This may be desirable during a surgical operation, for example, where a blood vessel or other tubular structure needs to be temporarily or permanently closed off. A clip or clamp device may be used for this purpose.

Many situations require the closure of the tubular structure to be temporary, in which case, for blood vessels, it can be important to allow blood to again flow normally through the vessel once it is allowed to re-open. It can also be advantageous to avoid damage to the blood vessel during its closure, for example due to excessive compression, roughness or piercing.

One prior technique relates to a method for laparoscopic anastomosis (RU 2241391, published 12 Dec. 2004), in which a chilled sterile clip is set within the lumen of the conveyor by opening the clip jaws into a V-shape and fixing them with their rear projections. The clip is delivered and placed into the prepared holes by loosening it with the conveyor's traction with the pusher's support. When heated the clip closes its jaws and compresses the walls of hollow organs. A disadvantage of this method is its limited functionality i.e. failure to recover the blood flow in the tubular hollow elastic organ (the "vessel").

Another technique relates to a method of clipping elastic tubular structures (RU 2213529, published 10 Oct. 2003). This method is executed via the compression of an organ by a clip made of a biologically inert alloy with a one-sided and reversible shape memory effect. Before applying, the clip is deformed at a temperature below the implantation temperature to give it an easy to install shape. The tissue is stitched with the pointed end of the clip; the clip is positioned at an application site to close the lumen (cavity) of the vessel. The clip is removed at a temperature below the implantation temperature as the clip partially opens.

A disadvantage of this method is the limited time left for manipulation and installation of the clips, as the clip's jaws are closed when reaching the temperature of the clip, which is close to the body temperature. Additionally, piercing of the tissue with a pointed end of the clip is required for secure fixation of the clip, which is unacceptable for operations on thin vessels. Also this method implies that a fairly significant cooling of body tissues, where the clip is applied, is required to remove the clip, which can either have serious consequences or can be difficult to implement.

Another technique involves a clip for anastomosis of hollow organs (RU 2285468, published 20 Oct. 2006). The clip contains a double-coil long wire. The spiral is clamped along its entire length to ensure compressive interaction and has loose wire ends at one end of the spiral, which is made from a nickel-titanium alloy (NiTi) with shape-memory effects and super elasticity. Both wires of each coil of the spiral at mostly the second end of the spiral are straightened and closed together to reach mutual contact and form the linear wires. The result is the extension of the application area due to anastomosis of small hollow organs without making extensive holes, causing injury or violating their physiology.

A deficiency of these clips is the invasiveness of the anastomosis procedure as additional piercing of the tissue is needed using ligatures. Also there is no procedure for removing the clip without causing additional trauma.

Another technique involves a clip (RU 2213529, published 10 Oct. 2003) formed of biologically inert material with a single and reversible shape memory effect, which allows the clipping of vessels and tubular organs as well as fixing the tissues via stitching at the same time. The clip can later be removed if necessary, as in the case of cavity and laparoscopic procedures. The clip is comprised of a rounded or flattened jaw that is bent so that one side forms a circular or elliptical loop, and the other side forms two parallel jaws, closely adjacent to each other, of which at least one has a bent ear in the form of a ski. There are notches on the inner side of the jaws, providing a reliable self-locking mechanism of the clips on a frame.

A deficiency of these clips is their lack of secure fixation on tubular organs and the inherent risk of slipping during organ pulsation or accidental mechanical contact with surgical instruments. Other disadvantages are inherent in the complexity of procedures for their application and removal.

Another technique involves a surgical manipulator (RU 2109488, published 27 Apr. 1998), in which the working end of a manipulator moves a pair of jaws, with the ability to open and close them. A guide node is movably mounted at the opposite end of the manipulator, and is able to interact with the transmission of the fixation and implantation mechanism. The tubular frame of the manipulator is covered with an electro-insulating layer and contains a cavity for a cooling element. The manipulator provides for a thermo-element to be embedded in the frame's cavity, which works through a thermo-electric Peltier effect cooling the compression element with thermo-mechanical shape memory.

Disadvantages of the device are in the difficulties with the design: invasiveness of the device and the inability to remove the stitching elements. Peltier elements are used for maintaining the permanent low temperature of the stitching elements in order to preserve their elastic state at the time of delivery and release. Such design leads to rapid overheating of the Peltier elements and the possible premature release of the shape memory effect, before the stitching elements are reset. Another disadvantage of this device is that shape memory elements can only be used once; it is also impossible or at least impractical to adjust them once they have been applied in cases of improper application to the connecting tissues.

Another technique involves a device for applying gripping clips (RU 2362498, published Jul. 27, 2009), which contains a stem with working branches, a feeding mechanism in the form of a movable cover, a transmission with a frame and a plate on the inner surface of which are the jambs, the height of which is a multiple of the clip's length. The plate with the jambs is secured at the distal end of an additional surface of the stem with sponges. The plate is able to move relative to the stem. It is also spring-loaded on the other side into the movable cover. The movable cover is spring-loaded by the additional spring installed at the stem with sponges on the transmission's side. A fixed sleeve is installed between the springs, and a movable sleeve is installed at the distal end. Dimensions of the movable sleeve are chosen so as to ensure its interaction with the protrusions, made on the inner surface of the movable frame. Mounting surfaces in the form of grooves and jambs for the initial installation of the plates are installed at the distal end of the movable frame.

A disadvantage of this device is that the stitching elements can only be used once and can be difficult to remove without trauma. It is also not practical to use this device for clipping vessels due to increased trauma and the risk of bleeding.

Another technique involves a device for applying gripping staples (RU 2052979, published Jan. 27, 1996), which includes a frame with mounting surfaces for the staple depot, working sponges, a transmission and a feeding mechanism. The feeding mechanism is connected to the frame with guide slots and spring-loaded handles installed in those slots. The handles are attached to an enclosure placed inside the cover, which contains a supporting surface and see-through holes. A movable lid is installed at the end of the cover, on the inner surface of which are the jambs, the height of which is a multiple of the staple's length. The jambs are able to interact with the supporting surface and see-through holes. A counting mechanism for gripping staples is installed on the outer surface of the cover. The frame of the feeder mechanism is designed as a movable part of the transmission, which is equipped with terminal clamping surfaces, which are able to rotate the sponges.

A disadvantage of this device is that the stitching elements can only be used once and can be difficult to remove without trauma. It is also impractical to use this device to clip vessels due to increased trauma and the risk of bleeding.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to a clip comprising:
a base portion;
first and second opposed arms coupled to the base portion; and
first and second opposed jaws coupled to the respective first and second arms, the first and second opposed jaws each having an inwardly extending portion that extends towards the base portion;
wherein at least the base portion is formed of a shape memory alloy tending to force the first and second arms toward each other when a temperature of the base portion meets or exceeds a transformation temperature of the base portion.

The inwardly extending portion of each of the first and second opposed jaws may have an inner end that curves toward the respective first and second arms. An outer surface of the clip along the base portion and the first and second opposed arms may be generally smooth. The clip may be formed of biologically inert materials.

The first and second jaws may each have end portions extending away from the base portion, the end portions having rounded tips. The first and second jaws may be separable to adopt an open position in which the jaws are acutely angled relative to each other. In the open position, the jaws may not contact each other. When a shape memory of the base portion is activated by heating the base portion, the base portion may tend to force the first and second jaws toward a closed position. In the closed position, the inwardly extending portions may not contact each other. At least the base portion may be formed of nitinol. The clip may be a surgical clip.

The base portion, the arms and the jaws may comprise the same material. The base portion, the arms and the jaws may be integrally formed. The first and second jaws may have perturbations formed along at least part of a generally straight inner engaging surface.

The base portion may define at least one land for contact with a temperature modification element. The at least one land may comprise opposed lands and the clip may be held for surgical application by gripping the opposed lands.

Some embodiments relate to a cartridge comprising a plurality of the clips described herein. The plurality of clips may be held in the cartridge in an open position.

Some embodiments relate to a kit comprising at least one of the clips described herein or the cartridge described herein and further comprising a clip manipulator, the clip manipulator comprising:
at least one arm to hold one clip; and
at least one thermoelectric transducer to impart a temperature change to the base portion of the clip sufficient to cause the temperature of the base portion to meet or exceed the transformation temperature. Some embodiments relate to the clip manipulator as described above on its own.

In the kit, the at least one arm may comprise two arms. In the kit, the at least one thermoelectric transducer may be coupled to a distal end of the or each at least one arm. In the kit, at least one thermoelectric transducer may be operable to cool or heat the base portion. In the kit, the at least one thermoelectric transducer may comprise at least one Peltier element.

In the kit, the at least one arm of the clip manipulator may comprise a distal pair of opposed jaws arranged with one thermoelectric transducer on each jaw, wherein the opposed jaws are useable to simultaneously grip the base portion of the clip and impart the temperature change thereto.

Some embodiments relate to a clip, comprising:
opposed jaws, each jaw having opposed first and second free ends and defining respective opposed clamping surfaces; and
a coupling portion joining the opposed jaws, the coupling portion being coupled to each jaw at a location intermediate the free ends, wherein the coupling portion is formed of a shape memory alloy so that the coupling portion causes relative movement of the jaws in response to a change in temperature of the coupling portion.

Embodiments generally relate to a new method and new tools that can be used for creating artificial reliable haemostasis in hollow tubular organs while preserving the integrity of their internal structures. Embodiments aim to reduce or eliminate excessive thrombus formation and restore blood flow in a hollow tubular body after exposure to artificial haemostasis.

Some embodiments relate to a clip made of memory shape alloy that helps to increase the reliability of haemostasis reduces the risk of a clip accidentally slipping from a hollow tubular organ, and lowers trauma caused when using the clip.

Additionally, the surgical and the endoscopic manipulators described herein may solve additional technical challenges. Firstly, they may expand the functionality of a surgical and an endoscopic manipulator, as the delivery, manipulation application, removal and extraction of clips are executed with a single device, eliminating the need to use multiple tools. Secondly, they may reduce labour intensity and trauma when working with a manipulator, as well as simplifying and improving the reliability of the manipulator.

Some embodiments relate to a method of closing a tubular organ, for example to create haemostasis (i.e. stopping blood flow in a vessel), using the described clip by applying heat to the clip to cause it to close according to its shape memory. The method may further involve the application of cooling to the clip to cause it to at least partly open from its closed position and allow it to be removed, thereby allowing a lumen of the organ to open again and allow fluid flow. The heating and cooling may be applied using the same thermoelectric transducer elements on the same device. Methods to create haemostasis and restore blood flow in tubular elastic organs, as well as the devices to implement such methods (medical clip, surgical manipulator and endoscopic manipulator), are explained below.

The haemostasis and restoration of blood flow in tubular elastic organs can be created by means of a clip as described herein, delivered to an application site with a manipulator. The manipulator holds the clip by its ear via a mechanical contact with the manipulator's working surfaces. The contact has to be made with at least one Peltier element located in a distal end of the manipulators' jaws. This method enables tubular elastic organs to be deformed under pressure via counter-movement of the working surfaces of the clip's jaws. The jaws have previously been spread-out, at a temperature below the onset temperature of martensitic transformation in the material (transformation temperature) of the clip's ear. The pressure is generated by transferring force and momentum to the clip's jaws via the clip's ear. Reactive voltage (stress-induced movement) is generated in the material of the clip as a result of the shape memory alloy effects, which activate as the temperature of the clip's ear rises via a thermal contact with the working surface of the Peltier elements, which were pre-heated. Then the direct contact the clip's ear and the working surface of Peltier elements is eliminated. However, as the clip's ear cools to reach the body temperature, sufficient compression in the application site of a tubular elastic organ is maintained to support haemostasis. The blood flow in the vessel can then be restored by forming a lumen in the tubular elastic organ. This lumen forms when the pressure from the clips' jaws drops and they partially open, which is a result of the temperature of the clip's ear material dropping below the temperature of the onset of martensitic transformation (transformation temperature), which occurs when the clip's ear contacts the working surface of the Peltier elements, which are switched to their cooling mode.

In some embodiments, the medical clip is made of a biologically inert material compatible with living tissue and contains an ear, the end of which is connected with two jaws via two arches. Proximal ends of the jaws are located in the space between the arches. The clip's ear is made of a shape memory alloy.

Some embodiments relate to a surgical manipulator that contains upper and lower elastic jaws arranged one along each other with a gap and interconnected by their proximal ends. The surface of at least the distal parts of the upper and lower elastic jaws is made of a biologically inert material. Transverse dimensions of these jaws are smaller than their longitudinal dimensions. Peltier elements are located at the distal ends of at least one of the jaws. These elements are connected to a power supply through conductive electrical insulated wires placed along the elastic jaws via at least a three-position switching block of Peltier elements.

Some embodiments relate to an endoscopic manipulator that has two elastic jaws, at least one of which is movable. The elastic jaws are mounted at the distal end of the manipulator; their surface is made of a biologically inert material. The Peltier elements are fixed at the loose ends of at least one of the jaws. These elements are connected to a power supply through conductive electrical insulated wires placed inside an elastic hollow rod with a rotation mechanism, which is mounted between the proximal end of the rod and its handle. Peltier elements are connected via at least a three-position switching block. The other ends of the elastic jaws are crossed over in the first connecting node, which is installed at the distal end of the hollow elastic rod. The first connecting node is joined with a pulling rod passed through the elastic hollow rod and movably connected with the rear handle, which is movably connected with the front handle via the second connecting node. One end of the rack mechanism is mounted at the rear handle and is passed through a hole in the front handle, the other end of which is equipped with a pressure plate.

Some embodiments relate to a method to create haemostasis to restore blood flow in the tubular elastic organs, with specific devices to implement this method (medical clip, surgical manipulator and endoscopic manipulator). The haemostasis to restore blood flow in the tubular elastic organs is created by means of a clip, delivered to an application site with a manipulator. The manipulator holds a clip by its ear via a mechanical contact with manipulator's working surfaces. The contact has to be made with at least one Peltier element located in distal ends of the manipulators' jaws. This method implies that tubular elastic organs are deformed under pressure via counter-movement of the working surfaces of the clip's jaws. The jaws have previously been spread out in a temperature below the onset temperature of martensitic transformation in the material of the clip's ear. The pressure is generated by transferring the force momentum to the clip's jaws via the clip's ear. Reactive voltage is generated in the material of the clip as a result of the shape memory alloy effects, which activates as the temperature of the clip's ear rises via a thermal contact with the working surface of Peltier elements, which were pre-heated. Then the direct contact the clip's ear and the working surface of Peltier elements is eliminated. However, as the clip's ear cools to reach the body temperature, sufficient compression in the application site of a tubular elastic organ is maintained to support haemostasis. Further, the blood flow is restored by forming a lumen in a tubular elastic organ. This lumen forms when the pressure from the clips' jaws drops and they partially open, which is a result of the temperature of the clip's ear material dropping below the temperature of the onset of martensitic transformation, which occurs when the clip's ear contacts the working surface of Peltier elements, which are switched to the cooling mode.

The preliminary opening of the clips' jaws may be performed at a temperature below about 20° C. The shape memory effect in the material of the clip's ear may take place at temperatures above about 35° C. within about 0.1-10 sec. The blood flow may be fully or partially restored as a lumen is formed within a tubular elastic organ. The clip's jaws may partially open to restore the blood flow at a temperature below about 20° C. within about 0.1-10 sec.

BRIEF DESCRIPTION OF THE DRAWINGS

The invention is illustrated via the following drawings:

FIG. 4 is a schematic side-sectional view of a surgical manipulator for applying the clip of FIGS. 1, 2A to 2C and 3A to 3E, including a switching block on the surgical manipulator;

FIG. 5 is a schematic side-sectional view of a further embodiment of the surgical manipulator for applying the clip of FIGS. 1, 2A to 2C and 3A to 3E, including a remote installation of the power supply and a switching block;

DETAILED DESCRIPTION

Described embodiments relate generally to metallic clips, such as surgical clips, and manipulation devices therefore. Such embodiments may be applied generally to open and endoscopic (laparoscopic) surgery. Embodiments can be used for such operations as cholecystectomy, appendectomy, gastrectomy, hemicolectomy, fund-application, cardiovascular and other operations which require tissue clipping or clamping in vessels.

As used herein, the term "proximal" is a relative term intended to refer to a location, direction or position closer to the operator of the manipulation device. Thus, as applied to the clip described herein, the term "proximal" is intended to indicate parts of the clip near or adjacent the base or "ear" of the clip. In contrast, the term "distal" is a relative term having an opposite connotation to "proximal" and intended to refer to a location, direction or position away (or extending away) from the operator of the manipulation device. As applied to the clip described herein, the term "distal" is intended to indicate parts of the clip further away from the base or "ear" of the clip.

Figure 1:
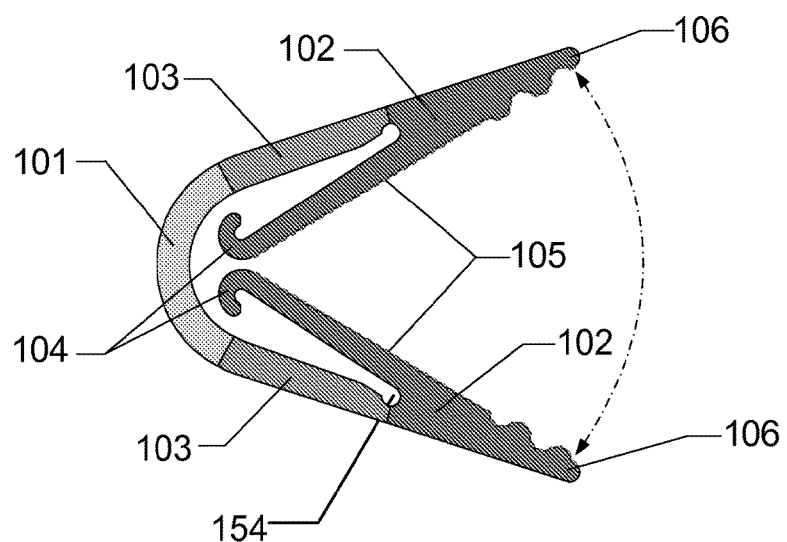
FIG. 1 is a schematic representation of a medical clip according to some embodiments.

The medical clip 100 in FIG. 1 comprises an ear 101, a pair of jaws 102, arches 103, a proximal ends of the jaws 104, a pair of jaws working surfaces 105, a distal ends of the jaws 106 (for conductive connection to) a pair of Peltier elements and a light signaling device 111.

A surgical manipulator 151 is shown in FIGS. 4 and 5 comprising an upper jaw 107, a lower jaw 108, a distal end 109, Peltier elements 110, a light signalling device 110, a button of forced heating 112, a micro switch of forced heating 113, a button of forced cooling 114, a micro switch of forced cooling 115, a mechanism for jaw fixation 116, a thrust wedge 117, a slider 118, a guide groove 119, guides of the slider 120, a power source 121, a screw connection 122, grooves for wiring 123, an electrical connection 124, an electrical socket 125, a proximal end 126, an electrical cable 127 leading to a foot pedal to switch modes (not shown).

Figure 7:
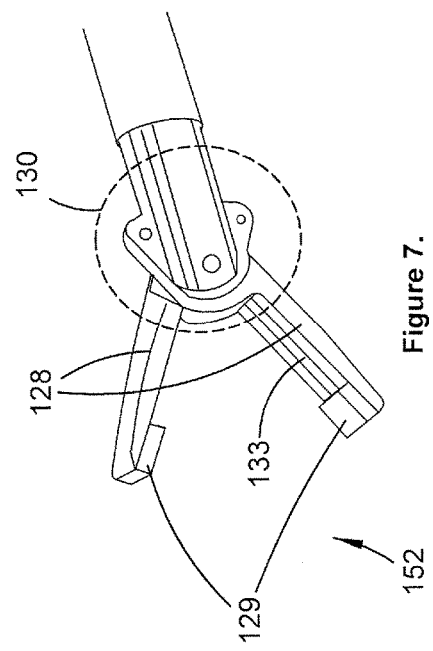
FIG. 7 is an enlarged perspective view of a distal end of the endoscopic manipulator of FIG. 6.

The distal end of an endoscopic manipulator 152 is shown in FIG. 7, which comprises of a pair of jaws 128, Peltier elements 129 and a first connecting node 130 and insulated conductive wires 133.

Figure 6:
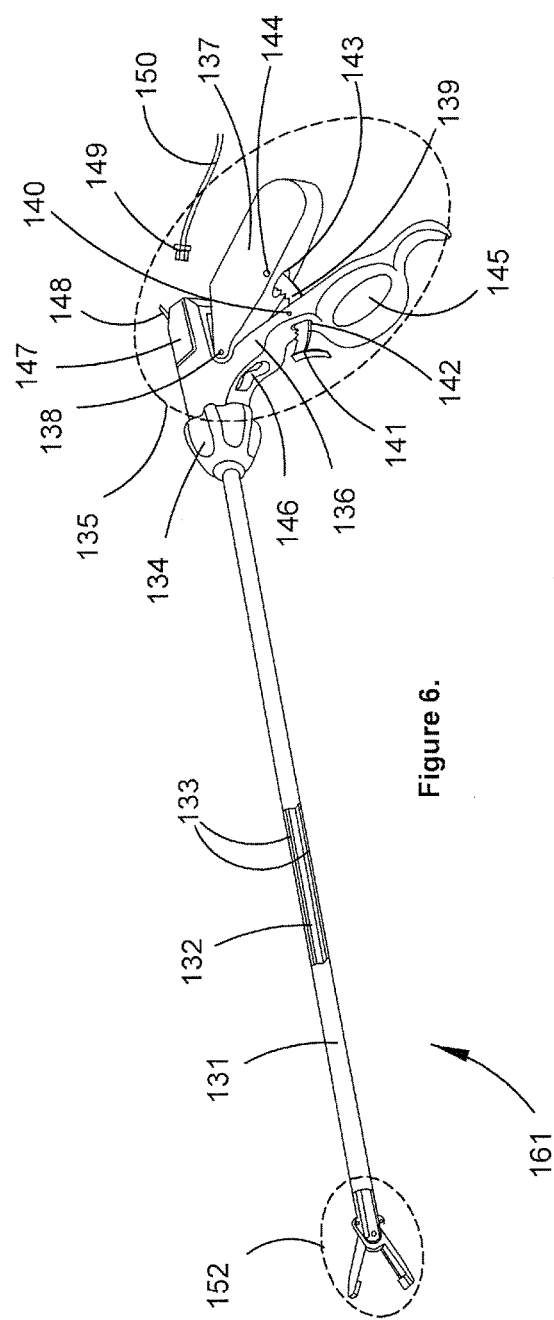
FIG. 6 is a perspective view of endoscopic manipulator for applying the clip of FIGS. 1, 2A to 2C and 3A to 3E.

An endoscopic manipulator 161 is shown in FIG. 6 which comprises a distal end of the manipulator 152 A hollow elastic rod 131, a pulling rod 132, conductive electrical wires 133, a rotation mechanism 134, a handle 135, a front handle 136, a rear handle 137, a second connecting node 138, a rack mechanism 139, a jamb for the rack mechanism 140, a pressure plate 141 for the rack mechanism, a through hole 142 in the front handle, a mounting groove 143 in the rear handle, a mounting rod 144, a hole for fingers 145 in the front handle, a button 146 to switch the block of Peltier elements, a power supply 147, a proximal tip 148 of an electrical connector, a socket 149 for the electric connector, an electrical supply 150 leading potentially to a foot pedal for switching the block of Peltier elements (not shown), equipped with a power supply, signalling lights and/or an audio device (not shown).

Described embodiments generally relate to a new method and new tools for creating artificial reliable haemostasis in hollow tubular organs while preserving the integrity of their internal structures. Embodiments aim to reduce or eliminate excessive thrombus formation and allow restoration of blood flow in the hollow tubular bodies exposed to artificial haemostasis. Each embodiment may solve a specific set of medical problems.

Specifically, the clip made of one or more memory shape alloys, may help to increase the reliability of the haemostasis, may reduce the risk of accidental clip slippage from a hollow tubular organ, and may lower trauma when using a clip.

Additionally, the surgical and the endoscopic manipulators 151, 161 may address further technical challenges by:

Improving the functionality of a surgical 151 and an endoscopic manipulator 161, as the delivery, manipulation application, removal and extraction of clips 100 can be executed with a single device, eliminating the need to use multiple tools.

Reducing labour intensity and trauma when working with a manipulator 151/161 as well as simplifying and improving the reliability of a manipulator 151/161.

The method to create haemostasis and restore blood flow in a tubular elastic organ, as well as the devices to implement this method (medical clip 100, surgical manipulator 151 and endoscopic manipulator 161), are explained below.

The haemostasis and restoration of blood flow in a tubular elastic organ 153 can be created by means of the clip 100, delivered to (and optionally removed from) an application site with a manipulator 151/161. The manipulator 151/161 holds the clip 100 by its ear 101 via a mechanical contact with manipulator's working surfaces (upper jaw 107 and lower jaw 108). The contact has to be made with at least one Peltier element 110 located in distal ends of the manipulators' jaws 107/108. This method implies that tubular elastic organs 153 are deformed under pressure via counter-movement of the working surfaces of the clip's jaws 102. The jaws 102 have previously been spread out at a temperature below the onset temperature of martensitic transformation (transformation temperature) in the material of the clip's ear 101.

A plurality of clips 100 may be stored together in a metal or plastic cartridge (not shown) of, say 10, 15, 20 or 30, clips 100. When in the cartridge, the clips 100 are in the open position and are preferably cooled to a temperature below their martensitic transformation temperature so that they do not clamp onto the cartridge body and can be removed from the cartridge. This cooling may be effected by use of the manipulator 151/161 or by storing the cartridge in a cooling chamber.

The pressure is generated by transferring the force momentum to the clip's jaws 102 via the clip's ear 101.

This clamping/clipping pressure generated by clip 100 is not maintained through reliance on the shape-memory alloy. Once the clip 100 is in position the mechanical strength of the clip 100 is sufficient to hold it in a closed position, that is, there is no reliance on the application of temperature to maintain the clip ear 101 above its transition temperature.

Reactive pressure is generated in the material of the clip 100 as a result of the shape memory alloy effects, which activate as the temperature of the clip's ear 101 rises via thermal contact with the working surface of Peltier elements 110, which are pre-heated. When the direct contact between the clip's ear 101 and the working surface of Peltier elements 110 is eliminated, and the clip's ear 101 cools to reach the body temperature, sufficient compression in the application site of a tubular elastic organ 153 is maintained to support haemostasis. Further, the blood flow is restored by forming a lumen in a tubular elastic organ 153. This lumen forms when the pressure from the clips' jaws 102 drop and they partially open, which is a result of the temperature of the clip's ear 101 material dropping below the temperature of the onset of martensitic transformation (transformation temperature), which occurs when the clip's ear 101 contacts the working surface of Peltier elements 110, which are switched to the cooling mode. When the clip's ear 101 is sufficiently cooled, the clip 100 will at least partially open, although it may not re-open as far as it was previously opened prior to its closure.

Preliminary opening of the clips jaws 102 is conducted at a temperature below 20° C. The shape memory effect in the material of the clip's ear 101 takes place at temperatures above 35° C. within a time frame of about 0.1-10 sec. Full or partial restoration of blood flow is done as a lumen in the tubular elastic organ 153 forms. Partial release of the clip's jaws 102 restores blood flow at a temperature below about 20° C. within a time frame of about 0.1-10 sec.

The medical clip 100 is made of a biologically inert material compatible with living tissue and contains an ear 101, the end of which is connected with two jaws 102 via two arches 103. Proximal ends of the jaws 104 are located in the space between the arches 103. The clip's ear 101 is made of a shape memory alloy.

The ear 101 of the clip 100, in particular, is made of a medical nickelide-titanium alloy (NiTi). The clip's ear 101 can have various forms such as: semi-circular, elliptical, U-shaped, or zigzag as shown in FIGS. 3A, 3B, 3C, 3D, and 3E. The maximum allowable angle of open jaws 102 and the level of the average compressive force of the clip are determined by the shape and size of the clip's ear 101.

The proximal ends of the jaws 104 are located in the space between the arches 103 and the ear of the clip 101. Both clip's jaws 102 can either have the same or different length, ranging in size from about 2 mm to 50 mm. The thickness of the two clip jaws 102 can also be either the same or different.

By varying the thickness of the jaws 102 and the ear 101, differing levels of compressive mechanical force can be achieved, allowing different clips to be tailored for different sizes and strengths of organ. The length of the jaws 102 may also be varied depending on the size, shape and strength of the organ to be clipped. For each embodiment of clip, a range of sizes is contemplated, allowing the surgeon to select a suitably sized clip for the procedure.

The entire working surface 105 of the jaws 102, or only localised parts, has either a straight smooth or wavy smooth, or wavy rough frontal shape. The entire working surface 105 of the jaws 102, or only localised parts, have either straight or angled incisions. The entire working surface 105 of the jaws 102, or only localised parts, have either straight or angled projections.

The length of the clip's arches 103 do not exceed the length of the respective clip's jaws 102, and the thickness and width of the arches 103 are dependent on the thickness and width of the ear of the clip 101.

The proximal ends 104 of the jaws 102 are illustrated in FIG. 1. In the illustrated embodiments, the ends 104 have been curved and rounded and face outwards within the internal curvature of the ear 101. In this curved formation of proximal ends 104, the possibility of the tubular organ 153 being caught or snagged by the inner proximal ends 104 is minimised. This may not be a concern once the clip 100 is in place, however on removal of the clip 100, it is possible that the organ 153 may extend towards the proximal ends of the jaws 104 and, if the proximal ends 104 were sharp rather than rounded, the tubular organ 153 may become caught or trapped as the clip 100.

The working surfaces 105 (i.e. those surfaces that engage and compress the tubular organ 153) of the jaws 102 may have various different patterns of undulations, ridges or teeth, depending on the application for the clip. These can be seen illustrated on the working surfaces 105 of the jaws 102 in FIG. 1. These undulations, ridges or teeth assist the clip 100 by providing additional friction or gripping ability, both in a lateral and horizontal direction (where the main mechanical force applied by the clip 100 is in the vertical direction). This additional friction can be advantageous in preventing the clip 100 from being moved out of position, either by surgical instruments, or by the pulsation of the tubular organ 153 itself.

The contouring of the working surfaces 105 of the jaws 102 is intended to provide generally even spreading of mechanical loads across all or most of the length of the working surfaces 105, and to avoid point loads and pin-point pressure on any localised area of the tubular organ 153. As the ear 101 begins to close and adopt its memorised shape, the arches 103 transmit the translation to the jaws 102 and the working surfaces of the jaws 105 travel towards each other. As the working surfaces 105 contact the tubular organ 153, the organ begins to compress and increases the surface contact with the clip 101. Slight flexion of the jaws 102 may occur near where the arches 103 transition to jaws 102 as the clip 100 is closed. Uneven load distribution on the tubular organ 153 could cause damage to part of the organ 153, so the shape and dimensions of the clip are selected to allow the working surfaces 105 to adopt a spaced apart, generally parallel configuration in the closed form. This is intended to mitigate the possible pinching of the organ 153

In some embodiments, the clip 100 may have a circular or rounded cut-out 154 where each arch 103 transitions distally into the jaw 102, as illustrated in FIG. 1. The cut-out 154 may be formed partly in the jaws 102 and partly in the arches 103, adjacent to the working surfaces of the jaws 105. This cut-out has forming benefits for the manufacture of the clip 100 and may also reduce the possibility of uneven load distribution, by avoiding having an excessively thick portion in the middle of each jaw 102. If the cut-out 154 were absent, this may lead to the ends of the jaws 102 having a relatively stiff centre section and more flexible ends, thus increasing the possibility for excessive loading of the organ 153 at the proximal end of the jaws 104.

The lateral width of the clip 100 (i.e. in a direction into the page, as seen in FIG. 1) may vary but should generally be sufficiently wide and/or sufficiently rounded at its lateral edges to avoid or at least minimise the clip 100 having a cutting effect on the tissue that it clamps. This cutting effect may also be minimised by instilling a shape memory in the clip 100 that does not cause the jaws 102 to fully close and instead allows a small gap therebetween in the closed position.

The level of distribution of the compressive force along the length of the clip's jaws 102 is driven by the changing size of the arches 103, as well as the location of their contact with the jaws 102.

The entire clip 100 may be formed of a biologically inert shape memory alloy material, allowing the clip 100 to be left on the tubular organ 153 for lengthy or indefinite periods of time, if required. Alternatively, a biologically inert coating may be applied to reactive shape memory alloy materials, to reduce or eliminate short term corrosion issues. The clip 100 may be produced in different size, material and shape embodiments, depending on the nature of the operation (area of the body to be contacted) and the duration for which the clip 100 will remain in contact with the organ 153.

The surgical manipulator 151 contains upper 107 and lower elastic jaws 108 arranged one along each other with a gap and interconnected by their proximal ends. The surface of at least the distal parts of the upper 107 and lower elastic jaws 108 is made of a biologically inert material. In some embodiments a biologically inert coating may also be applied on a portion of the elastic jaws 107 and 108.

Transverse dimensions of these jaws are smaller than their longitudinal dimensions. Peltier elements 110 are located at the distal ends of at least one of the jaws 107/108. These elements 110 are connected to a power supply 121 through conductive electrical insulated wires 123 placed along the elastic jaws 107/108 via at least a three-position (heating/cooling/neither) switching block 112/114 of Peltier elements 110.

In addition, the proximal ends of the upper 107 and lower jaws 108 are joined at a connection point or region 122 via screwing, welding, soldering or gluing.

The upper 107 and lower jaws 108 in some embodiments are joined in a "tweezer" like manner, whereby the proximal ends closest to the surgeon's hand are permanently joined together, providing for a flexible hinge point, allowing the surgeon to manipulate (i.e. open and close) the distal ends of the jaws 107 and 108 relative to one another, with one hand if necessary. The upper and lower jaws 107, 108 are preferably biased to adopt a position in which they are slightly apart, so that in this relaxed open condition, the jaws can be positioned around the ear 101 of a clip 100 and then gently squeezed together to adopt an inwardly compressed position and grasp the ear 101 (with the jaws 102 extending distally away from the manipulator) for application of the clip 100 as desired.

Transverse (width) dimensions of the upper 107 and lower jaws 108 may be of variable value along its entire length.

Peltier elements 110 are fixed by soldering or screwing. A preferred method of attaching the Peltier elements 110 is to solder or screw them in place permanently to the jaws 107 and/or 108 although other methods of attachment may be contemplated, such as adhesives, welds, pins or nails, for example.

Power supply 121 mechanism sources either AC or DC electrical current. The power supply 121 in either manipulator 151, 161 may be derived from an external AC or DC source and optionally converted into a DC supply by circuitry within the manipulator 151, 161 for DC control of the Peltier elements.

The block of switching modes for Peltier elements can be made as a button of forced heating 112 and a button of forced cooling 114, installed in the middle of one of the jaws 107/108, opposite of which (on the other jaw) there is a micro switch for forced heating 113 and forced cooling 115, connected to power supply 121 mechanism installed at the distal end of the upper jaw 107.

Locating the button on one side of the jaws 107/108 and the micro-switch on the internal surface of the opposing jaw, allows a surgeon to activate said switches with a gentle and delicate movement, by squeezing the two jaws 107 and 108 together. The gentle and delicate action of these movements is preferable during a surgical procedure, as any sudden motion or jerking could cause trauma to the tubular organ 153.

The block of switching modes for Peltier elements can also be made as a foot pedal switch, equipped with a power supply 121 and connected to a surgical manipulator 151 through an electrical socket 125 mounted on the distal ends of the upper and lower jaws 107/108.

A foot-pedal switch actuator may allow the surgeon to have even more control over the surgical manipulator 161, without the distraction or potential interference of switches on the manipulator 161.

A mechanism for fixation of jaw 107/108 positions is located in the middle of the surgical manipulator 151. It consists of a moving slider 118, a thrust wedge 117, which is rigidly connected to the lower jaw 108 and freely passing through the hole in the upper jaw, guides 120 for the moving sliders 118 and the guide groove 119, located in the upper jaw 108. The moving slider 118 is located inside of the guide groove 119 and is rigidly connected to its lower part 120.

The fixing mechanism 116 enables the position of the upper jaw 107 and lower jaw 108 to be locked in place relative to one another. This allows the surgeon to release the jaws 107/108 and maintain control of the clip 100 while still in contact with the Peltier elements 110.

Surgical manipulator 151 can be equipped with a signalling light 111 and/or audio device.

The audio/visual signal may be used to alert the user to a change from forced cooling to forced heating, for example to alert when changes are made and/or to alert where inadvertent changes may have been initiated. The signalling light 111 may emit different colours to indicate different states, such as a blue light to indicate a cooling status or a red light to indicate a heating status, for example.

The endoscopic manipulator 161 shown in FIGS. 6 and 7 has two elastic jaws 128, at least one of which is made movable. The elastic jaws 128 are mounted at the distal end 152 of the manipulator; their surface is made of a biologically inert material. The Peltier elements 129 are fixed at the loose ends of at least one of the jaws 128. These elements are connected to a power supply 147 through conductive electrical insulated wires 133 placed inside the elastic hollow rod 131 with a rotation mechanism 134, which is mounted between the proximal end of the rod and its handle 135. Peltier elements 129 are connected via at least a three-position switching block. The other ends of the elastic jaws 128 are crossed over in the first connecting node 130, which is installed at the distal end 52 of the hollow elastic rod 131. The first connecting node 130 is joined with a pulling rod 132 passed through the elastic hollow rod 131 and movably connected with the rear handle 137, which is movably connected with the front handle 136 via the second connecting node 138. One end of the rack mechanism 139 is mounted at the rear handle 137 and is passed through a hole 142 in the front handle 136, the other end of which is equipped with a pressure plate 141.

A rotation mechanism 134 can be connected to the upper part of the front handle 136. The front handle 136 also contains holes 145 for fingers.

The rotation mechanism 134 allows the orientation of the clip 100 to be adjusted in order to adopt an appropriate position for ingress and egress to/from an internal surgical site and also for flexibility with the actual clip 100 attachment. The surgeon may release the clip 100 during an operation, if necessary, to re-orient the clip 100 in relation to the jaws 128. However, it may be preferable that the jaws 128 may be rotated using mechanism 134, and the clip be continuously retained by the jaws 128.

A flexible connection of the pulling rod 132 with the rear handle 137 is done with the help of a mounting socket, which is placed at the top of the rear handle 137 above the second connecting node 138. The head of the pulling rod 132 is inserted into this node 138.

The three-position switching block of Peltier elements 129 can be made as a micro switch of forced heating (similar to 113) and forced cooling (similar to 115), mounted at the front 136 or back 137 of the handle and connected to a power supply 150, located in the handle 136.

The three-position switching block of Peltier elements 129 may also be made as a foot pedal switch, equipped with a power supply and connected to the endoscopic manipulator 161 through an electrical socket 149 mounted on the handle.

The endoscopic manipulator 161 may be equipped with a signalling light and/or audio device to notify the user of which setting the Peltier elements 129 are on: hot or cold.

Reliable and damage-free haemostasis to restore blood flow in the tubular elastic organs 153 can be achieved by using the medical clip 100 with special instruments: a surgical manipulator 151 and/or endoscopic manipulators 161.

Embodiments are based on the principle of the mechanical action, such as deformation by pressing down, of elastic tubular organs, such as vessels, and fixation of such compressed position for a certain period of time. At the same, it is possible to restore the lumen within previously compressed elastic tubular organs. This possibility would greatly ease the work of the surgeon, and possibly shorten the duration of surgery.

In other words, pressing down on an elastic tubular organ 153 such as a blood vessel and fixing the vessel in a compressed position for a period of time using a clip 100, causes temporary haemostasis within the vessel. However, blood flow in the vessel may be restored on removal of the clip 100. It is further possible, using the clip 100 and with manipulator 151 or 161 to avoid substantial damage to a compressed organ, so that the lumen of the compressed elastic tubular organ can naturally restore itself. This ability is of great advantage to a surgeon, and may possibly shorten the duration of a surgery.

Deformation of an elastic tubular organ 153 is carried out with the help of the medical clip 100, made entirely or just having a stable coating of a biologically inert material compatible with human tissue. The use of such a material is necessary in order to minimise any bio-chemical (toxic, carcinogenic) health effects of the clips 100 on the body, which is especially important when the clip 100 is applied for a long time.

The clip's ear 101 or the entire clip 100 is made from a shape memory alloy, such as a medical nickelide-titanium alloy (NiTi). Its use is necessary to meet the specific mechanical (elastic-plastic, thermo-elastic and strength) characteristics of the medical clips 100, which are essential to achieve a reliable and secure haemostasis in tubular elastic organs 153 and to restore blood flow via a safe (and without the use of brute force) removal of the previously applied clip 100.

It is preferable that the clip 100 is removed as gently as possible, as any use of force in the removal of clip 100 may cause further damage to the organ 153 at the site of the temporary haemostasis.

The operating principle of the medical clip 100 is based on the shape memory effect. The effect reveals as follows. A shape memory alloy generally remembers its original or cold-formed shape (memory shape), such that the material may be deformed and mechanically twisted, but upon the application of heat, it will return to its memory shape. The temperature at which this transformation occurs is referred to as the transformation temperature or the temperature of Martensitic transformation, due the change in internal material phases. If the clip 100 is deformed excessively, out of its plastic zone and into elastic deformation, the shape-memory characteristics of the clip 100 may be damaged or lost and the clip may no longer transform between its open and closed positions with the application or removal of heat energy. The type of excessive deformation that would damage the shape-memory effect is not created by normal use of the clip as deformation under the shape-memory effect remains generally within the plastic zone of the material characteristics.

Figures 2A, 2B, 2C:
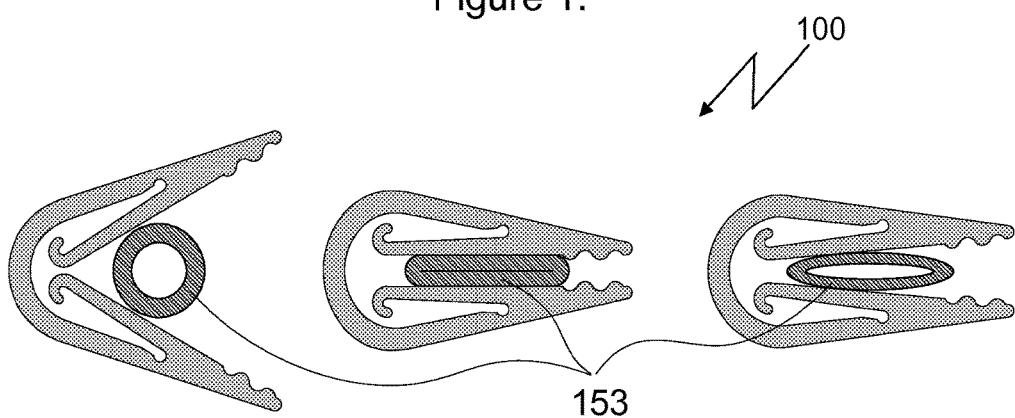
FIG. 2A illustrates the clip of FIG. 1 in an open (cocked) state, i.e. prior to being applied to a vessel.
FIG. 2B illustrates the clip of FIG. 1 in a closed state after being applied to a vessel and the vessel's compression.
FIG. 2C illustrates the clip of FIG. 1 in a partially opened state when the clip is being removed.
Figure 3A:
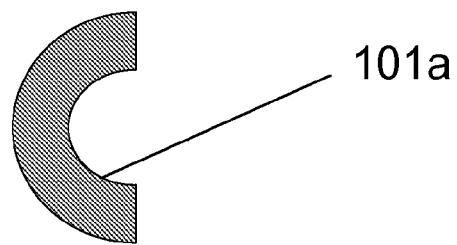
FIGS. 3A, 3B, 3C, 3D and 3E illustrate various different possible shapes of the clip's ear.
Figure 3B:
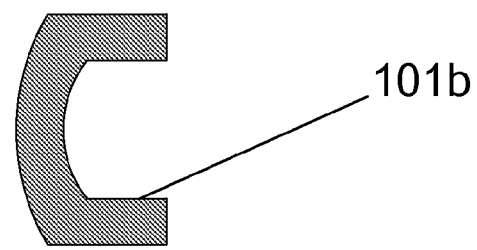
Figure 3C:
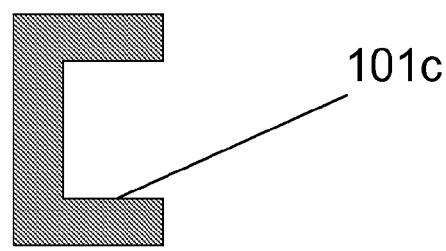
Figure 3D:
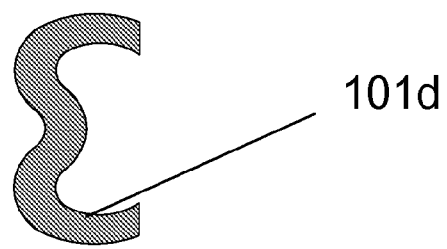
Figure 3E:
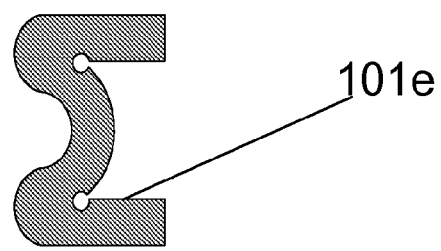

The clip 100 is cut from a sheet of shape memory alloy and is then subjected to a heat treatment. This gives the clip 100 a form suitable for transportation and application in the right place, which is achieved via plastic deformation. That is to say that the clip may be transported in its cold (open) form to the site of application and when heat is applied to the clip ear 101, it will return to its closed (memory shape) position. Variable sheet thicknesses can be employed for producing the clips 100 depending on what size and mechanical force is required to effectively compress and maintain haemostasis in the organ. When heated, the clip 100 will initially take a specified form (memory shape) of closed jaws 102 as shown in FIG. 2B), pressing down an elastic tubular organ 153. When the clip ear 101 is cooled, the clip jaws 102 will partially open up, as illustrated in FIG. 2C, which allows a trauma-free removal of the clip 100 or, if necessary, re-application of the clip 100.

Before application of the medical clip 100 to an organ 153, the clip 100 is put into a cocked (open) condition. The clip's ear 101 is pseudo-plastically deformed in advance, spreading the jaws 102 at a low temperature (below 20° C.) to give it a shape as shown in FIG. 2A, suitable for application to an organ 153.

Pseudo-plasticity is an effect where the austenitic phase of the material is stressed to induce the Martensitic phase. When the stress load is relieved the Martensitic phase returns to its Austenitic state and transforms back into its memory shape. While in this Martensitic phase the alloy is capable sustaining high levels of strain.

The opening of the jaws 102 is carried out at low temperature (below 20° C.) so that the material of the ear 101 achieves a temperature close to a temperature interval of martensitic transformation (transformation temperature range). At this temperature the material becomes flexible, its elastic modules are strongly decreasing, while its plastic deformation will be accumulating, up to certain limits, due to a reversible mechanism of accumulation of the plastic deformation, i.e. due to an oriented structural-phaseal transition caused by the external force.

Nitinol is a metallic alloy and as such is inherently flexible. Nitinol offers a favourable combination of physical and mechanical properties. Aside from its biocompatibility (a similar corrosion resistance to that of stainless steel), it is flexible (low Young's modulus of about 75 GPa), has a high UTS (about 750-960 MPa), displays biased stiffness characteristics (stiff in compressions and flexible in tension) and displays its super-elastic behaviour in a similar temperature range to the human body.

Nitinol's structure is a cubic crystal lattice configuration in its Austenite phase and is extremely strong. The austenitic structure transforms to a monoclinic crystal structure when the structure is cooled below the transformation temperature and the martensite becomes twinned within the nitinol. As the monoclinic structure is loaded, the martensite detwinns in the nitinol as it plastically deforms. If heat is then applied to the deformed nitinol, the crystal cubic configuration will realign, returning the nitinol to its cold-formed or memory shape. This whole loading and unloading cycle is repeatable, assuming that the mechanical deformation remains within the limits of plastic deformation.

Due to the heating and cooling reactions of nitinol and the complex bonding and transformation between martensitic and austenitic structures, there are four transition temperatures for a nitinol structure: the start and finish of martensitic formation within the austenite phase as the nitinol cools; and the start and finish of the austenitic formation within the fully martensite phase as the nitinol is heated up. With these properties, nitinol combines many of the advantages of a metal and a plastic into one material, allowing it to be flexibly manipulated into position with minimal risk of corrosion.

Before the surgery, the clips 100 are sterilized in a solution or they are treated in a gas steriliser for a prescribed statutory time period. The sterilisation process does not alter the clip's 100 desired properties, and can be repeated.

Alternatively, medical clips 100 can be stored in a sterile condition in a special container (cartridge) at a temperature no higher than 30° C. In the cocked (open) condition, the clip 100 is placed in a cartridge's socket, designed for storing one or several clips in a cocked state, for the duration of a surgery until a clip 100 needs to be used.

Maintaining the temperature in the cartridge during storage at no more than 30° C. is necessary to ensure that the clip jaws 102 do not close, which happens when the ear 101 reaches a temperature of about 35° C. or above.

The maximum allowable angle for the jaws 102 to spread (as shown in FIG. 1) is determined by the shape and measurements of the clip's ear 101. FIGS. 3A to 3E show a number of exemplary alternative ear shapes and configurations 101a, 101b, 101c, 101d, 101e. The smaller the width of the ear 101 and the greater the total length of its profile, the greater the maximum allowable angle for the working surfaces of the jaws 105 to spread (see FIG. 1).

A compressive force is required to close clip 100, this force is dependent on the size, shape, material and thickness of the clip 100. Increasing the width of the ear has a greater impact on the compressive force required to close the clip 100 than varying the thickness of the ear 101.

The level of the compressive force also depends on the size and shape of the ear 101. Increasing the width of the ear (more effect) or the thickness of the ear 101 can increase the level of the average compressive force.

During surgery, before applying the clip 100 to a flexible tubular organ 153, it is extracted from the cartridge in the following manner.

The clip 100 is grabbed by its ear 101, compressing it on both sides of the working surfaces or jaws 107/108 or 128 in contact with Peltier elements 110 or 129 placed on the distal ends of jaws 107/108 of the surgical manipulator 151 or the jaws 128 of the endoscopic manipulator 161 (depending on the type of surgery). While still holding the clip 100, it is pulled out of the sterile storage cartridge in the open position.

It should be noted that the clips 100 in the cartridge are sterile and stored in the open position ready for use in an operating theatre. The cartridges may stock multiples of a given size, shape and style of clip or a mixture of clips necessary for a given procedure.

When using the surgical manipulator 151, to secure a closed position the upper and lower jaws 107/108 for clamping the ear 101, the middle part of the jaws 107/108 is pressed by the surgeon's hands.

It is useful to be able to set the upper 107 and lower 108 jaws of the surgical manipulator 151 in place, to allow a surgeon to move their hand, vary the pressure on the jaws 107/108, change their grip or release the surgical manipulator 151 entirely. To set the jaws 107/108 in place, a fixation mechanism 116 may be used. The mechanism 116 comprises of a slider 118 and slider guide 119, a plurality of guides 120 and a thrust wedge 117.

The position of the jaws 107/108 is retained via a fixation mechanism 116 when the slider 118 is moved along the guide groove 119. This motion lifts the thrust wedge 117 which leads to jaws 107/108 closing.

When using the endoscopic manipulator 161, a closed position of the jaws 128 holding the clip's ear 101 is achieved by the pulling rod 132 stretching when the handles (front handle 136 and rear handle 137) come together. This motion is done by the surgeon's hand and the squeezed together position may be retained through the rack mechanism 139 and its associated jamb 140 fixing the relative position of the handle 136 and 137).

A surgeon inserts their finger in the finger hole 145 and rests the forefinger of the same hand on the pressure plate 141. This allows the two parts of the handle 135 to be gently squeezed together, forcing the rack mechanism 139 through hole 142. The rack mechanism 139 is attached to the rear handle 137 at a mounting groove 143 on the inside face of the rear handle 137. The rack mechanism is then fed through the hole 142 and terminated with a pressure plate 141 for the surgeon's finger to rest on. The rack jamb 140 can be used to lock the jaws 128 in their current location, allowing the surgeon an opportunity to adjust their grip of hand position without compromising the jaws 128 and their grip on a clip 100.

The clip 100 in a cocked position held by the manipulator 151/161 is led to the relevant site, such as a vessel 153 meant to be clipped.

When using an endoscopic manipulator 161, a special rotation mechanism 134 allows to manipulate (rotate) the clip 100 while it is held by the device (manipulator 161) and apply it to the relevant area.

The area of the organ 153 to be clipped is positioned between the working surfaces 105 of the jaws 102 (as shown in FIGS. 1, and 2), after which the medical clip 100 can be applied to the area 153.

The clip 100 can be applied without putting it under plastically deforming pressure. Instead, forced controlled pointed heating of above +35° C. of one of the structural elements of the clip ear 101. The ear 101 has no direct contact with clipped tissues 153.

The clip 100 may be applied without any mechanical loading of the clip ear 101. A controlled heating of the clip's ear 101 to a temperature of above about +35° C. is invoked to trigger the shape memory of the ear 101 into its memory position, which is closed. The ear 101 preferably does not directly contact the tubular organ 153, as this may cause further trauma to the area through the direct application of excessive heat.

The heating of the ear 101 is activated (initiated) by pressing the forced heating button 112 of the surgical manipulator 151. This affects the micro switch of forced heating 113. The same happens when pressing the Peltier button 146 on the handle 135 of the endoscopic manipulator 161 or pressing an appropriate pedal of forced heating on a pedal device of one of the manipulators, which should be held down for about 0.1-10 seconds.

The pressing of the buttons or other elements (to activate heating or cooling) as mentioned above leads to a short (0.1-10 second) closure of the electrical circuit from the power source 121/147. As a result, the electrical current of a particular polarity is applied to the light 111 and/or audible warning device 111, and heats the working surfaces of the Peltier elements 110/129.

The clip's ear 101, which has contact with the working surfaces of the Peltier elements 110, heats up as well. When the temperature in the material of the ear 101 reaches above about +35° C., reactive stresses are generated as the shape memory effect takes place.

Essentially the application of heat causes the clip 100 to revert to its closed position as the nitinol begins to revert to its purely austenitic cubic crystal configuration.

As a result of the shape memory effect, the clip ear 101 creates a force moment, which is transmitted to the jaws 102 of the medical clip 100 via its arches 103. A reciprocal movement of the jaws 102 deforms the tubular elastic organ 153, arising under the influence of the pressure in the working surface 105 of jaws 102. Within about 0.1-10 seconds of the ear's forced heating, the clip 100 is applied to the tubular elastic organ 153, closing the lumen inside the organ by clamping the jaws 102 (as shown in FIG. 2B).

After the jaws 102 are completely closed, the ear 101 is released to eliminate the direct thermal contact between it and the working surfaces of the Peltier elements 110/129. To do this when working with the surgical manipulator 151, the slider 118 is moved back along the guide groove 119, thereby releasing the thrust wedge 117.

When working with the endoscopic manipulator 161, the pressure plate 141 of the rack mechanism 139 is pressed on, thereby freeing it from its jamb 140, which results in a rotational movement of the rear handle 137 relative to the second connecting node 138, connecting it with the front handle 136.

The compression in place of the clip's application to the flexible tubular organ 153 is sufficient to maintain haemostatic effects, as the temperature of the ear 101 cools down to the ambient body temperature.

If the ear's cross-sectional area is in the range of about 0.1-2.0 mm$^2$, the ear 101 will be capable of generating the necessary compression of about 0.01-5 kg or equivalent force of 0.1-50N to clip different types of organs. The variety of clips 100 follows the anatomical classification of vessels (small, medium, medium-large and large-diameter) with its jaws 102 ranging from about 2 to 50 mm in length.

The proposed application of the medical clip 100 envisages the presence of the ear 101, and the jaws 102 made in special geometrical shapes (with grooves, waves, etc.), the work surface 105 and the arches 103. This design provides good lateral and longitudinal stability when applied to a tubular organ 153 as close contact with a high degree of uniformity of compression from the working surfaces 105 of the jaws 102 on the walls of a tubular body is established. The likelihood of unwanted clip slippage is minimised, which can happen under pressure inside a tubular elastic organ 153 when it pulsates and/or the clip 100 accidentally contacts surgical instruments.

The uniformity of compression further minimises the likelihood of unwanted clip slippage, and works in tandem with the undulations or teeth along the working surfaces of the jaws 105.

As a result, after the clip 100 is applied, a surgeon has an almost unlimited supply of time to perform the other phases of the operation. After that, depending on the surgical treatment, for example, if the clip is applied to a wrong site, or after completing other phases of the operation, the blood flow can be restored.

If the clip 100 is misaligned, or needs to be adjusted or even removed completely, the clip 100 can be removed and the blood flow in the vessel 153 can then be restored, naturally reforming the vessel lumen.

Restoration of blood flow is carried out by forming a lumen within the tubular elastic organ 153. To do this, the pressure from the working surfaces 105 of the jaws 102 is reduced as they open up partially (as shown in FIG. 2C). This happens as a result of the forced cooling of the clip ear 101 to a temperature below about +10° C. as martensitic transformation is activated in the material of the ear 101.

Once again, the ear 101 is grabbed by both sides of the working surfaces of Peltier elements 110 or 129, placed on the jaws 107/108 of the surgical manipulator 151 or jaws 128 of the endoscopic manipulator 161 (depending on the type of surgery) as they move towards each other. This movement is achieved in the surgical manipulator 151 when the surgeon's hands press on the middle part of the jaws 107/108. This movement is achieved in the endoscopic manipulator 161 when the surgeon's hands press on the handle 135 and its rear 137 and front part 136 come closer to each other as the pulling rod 132 stretches.

Forced cooling of the ear 101 is achieved when it thermomechanically contacts the working surface of Peltier elements 110/129. The Peltier elements 110/129 are transitioned into the cooling mode by clicking on the forced cooling button 114 in the surgical manipulator 151, which leads to the activation of a micro switch of forced cooling 115. When using the endoscopic manipulator 161 the forced cooling of the ear 101 is achieved by clicking on the Peltier button 146 of the endoscopic manipulator 161 or by pressing the pedal to the pedal control device (where applicable) and then holding it down for about 0.1-10.0 seconds.

The pressing of the button 114/146 or pedal as mentioned above leads to a rapid (about 0.1-10.0 sec) closure of the electrical circuit from the power source 121 or 147. As a result, the electrical current of a particular polarity is applied to the light and/or audible warning devices 111, and the working surfaces of the Peltier elements 110/129 begin to cool.

The ear 101 is cooled due to the thermal exchange with the cooled working surfaces of the Peltier elements 110/129. When the temperature in the ear's 101 material falls below about +10° C., martensitic transformation causes softening of the ear's 101 material and the jaws 102 begin to partially open. This allows for the removing of the clip 100 from the tubular elastic organ 153 with minimal trauma as the clip 100 is eased-off, being held (gripped) by its ear 101 and ultimately removed from the location of the surgical wound site.

The clip 100 can be reused if treated with a sterilising solution and/or kept in a gas sterilizer within the prescribed statutory time. The clips are then brought back into an open state with jaws 102 open ready for placement.

The proposed method of using these new advanced medical devices and instruments allows surgeries to have minimal traumatic effect on the fabric of the hollow tubular organs 153 of the body and provide for an increased accuracy of surgical interventions. These devices also greatly facilitate the work of a surgeon and may reduce the duration of surgeries.

As described herein, the Peltier elements function as a type of thermoelectric transducer or conversion element, converting electrical potential applied across the Peltier elements into a heating or cooling effect at an external surface of the Peltier elements.

Figure 8:
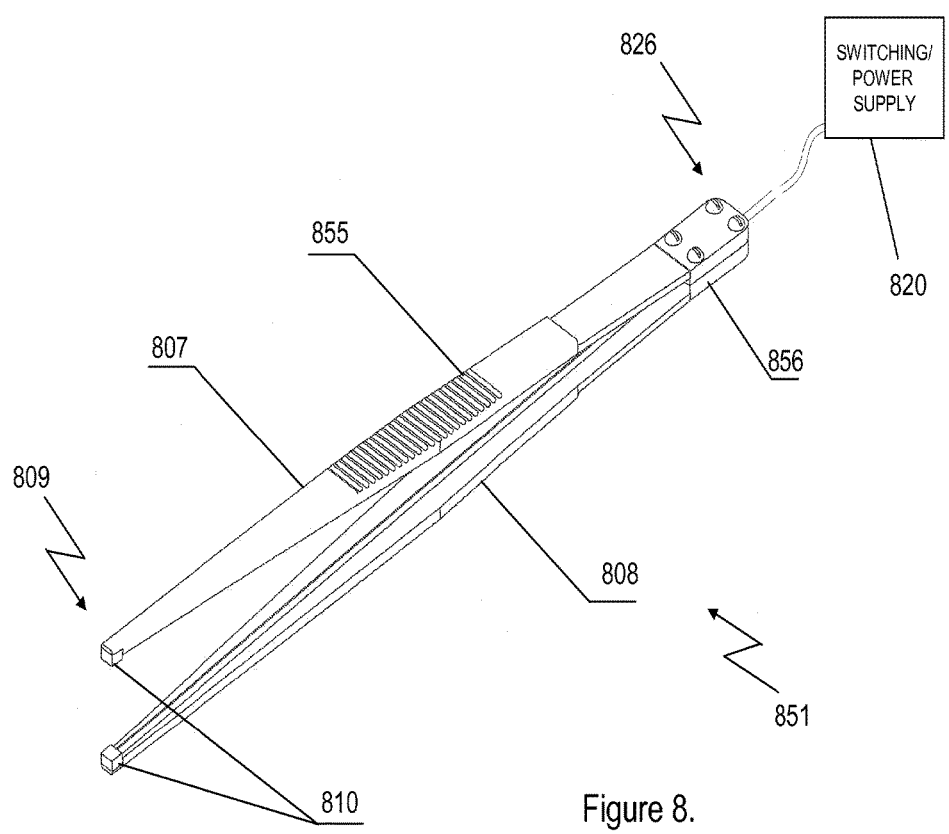
FIG. 8 is a schematic diagram in partial perspective view of a further embodiment of a surgical clip manipulator.

Shown in FIG. 8 is a clip manipulator 851 according to further embodiments. The clip manipulator 851 is similar in structure and operation to manipulators 151 shown in FIGS. 4 and 5. In particular, clip manipulator 851 has two opposed jaws or arms 807, 808 that are resiliently deflectable from an open position in which its distal ends 809 are separated, to a closed position, in which the distal ends 809 are closed together or closed around the lateral lands of the base portion/ear 101 of a clip 100. The arms 807, 808 are biased toward the open position by their shape and by a connector 856 that couples the arms 807, 808 together at their proximal ends 826. Clip manipulator 851 has at least one and preferably two thermoelectric transducer elements 810 (e.g. Peltier elements), with one each positioned at the respective distal ends 809 of the arms 807, 808 for applying a heating or cooling effect to the base portion/ear 101.

The clip manipulator 851 has a power supply and switching control unit 820 that is electrically coupled to the thermoelectric transducer elements 810 to supply the necessary control and current supply to the thermoelectric transducer elements 810. The power supply and switching functions of the power supply and switching control unit 820 may be provided separately from each other or within a single unit or housing.

The arms 807, 808 each have a gripping portion 855 in a middle portion thereof for easy gripping and manipulation of the manipulator 851 during application of the clip. Although not shown, the arms 807, 808 may have a clamping mechanism to allow them to be held in the closed position when they are closed about a base portion/ear 101 of a clip 100.

For each embodiment of manipulator described herein, it is at its core a manually manipulable clip delivery device that has the gripping/holding and temperature change functions co-located at the distal tip of the device. The device is thus readily usable as a heating/cooling device (to clamp and relax the clip 100) and a gripping/positioning device. Although the manipulator embodiments may in some instances be described with reference to the jaws or arms being elastic, this is intended to simply indicate that the jaws or arms of the manipulator are capable of a degree of flexion and/or relative movement at one or many points along their lengths, rather than being elastic in the sense of an elastic band. The jaws/arms of the manipulators may be relatively rigidly formed but with one or more pivot points and/or slider mechanisms allowing the jaws/arms to move relative to each other in order to grasp and hold the base portion/ear of the clip 100.

The clip embodiments described herein may be further described in the following terms. Clip 100 may be formed all or partly of a shape memory alloy, such as nitinol, with at least a base portion 101 being formed of the shape memory alloy. The base portion 101 has a flexible central part with opposed arms 103 extending in a C-shape or U-shape from each side of the central part. The central part may be curved, for example, in a convex or concave shape or may be at least partly straight, as illustrated by FIGS. 3A to 3E. At a minimum, the base portion 101 must be configured to adopt a shape memory when a suitable temperature change occurs to cause the material of the base portion 101 to move the opposed arms toward each other to adopt the memorised shape of the base portion 101.

The base portion 101 defines lateral lands on each lateral side, where the lands face outwardly in opposite directions that are generally perpendicular to a plane in which base portion 101 curves and moves under the influence of its shape memory. These lateral lands may be the flat side surfaces of the base portion 101. It is the lands that are intended to be gripped on each lateral side of the clip 100 by the thermoelectric transducers 110, 129 when positioning, heating or cooling the clip 100.

Together, the base portion 101 and arms 103 preferably have a rounded C-shape or U-shape. The arms 103 extend away from the base portion so that they form opposed arms movable relative to each other through an acute angle between open and closed positions of the clip 100. The arms 103 are coupled to the base portion 101, for example, by integrally forming the arms 103 with the base portion 101 or connecting them thereto by adhesion, welding or mechanical coupling, for example. Although the clip 100 as illustrated in FIG. 1 suggests a possible material or mechanical transition between base portion 101 and arms/arches 103 and between the arms/arches 103 and jaws 102, there may be no material or mechanical transition where the clip 100 is formed integrally, which is preferred. Thus, the transition may be notional, rather than physical.

With the base portion 101 of clip 100 acting as a proximal reference point, the arms 103 extend at least somewhat distally, with jaws 102 positioned at distal ends of the arms 103. The jaws 102 are coupled to the arms 103, for example, by integrally forming the jaws 102 with the arms 103 or connecting them thereto. Such connection of the jaws 102 with the arms 103 may be by adhesion, welding or mechanical connection, for example. An outside surface and profile of the base portion 101, arms 103 and jaws 102 may be generally smooth, optionally rounded at the proximal end and tapering toward a slightly rounded point at the distal end (at least when closed).

Clip 100 has two opposed jaws 102 that each extend towards a slightly rounded distal extremity of the clip 100. The jaws 102 thus have a distal end corresponding to the distal extremity of the clip 100 and also an inwardly extending portion acting as a proximal extension of each jaw 102. Each of the jaws 102 defines a tissue engaging surface 105 of sufficient lateral width and surface area that it does not tend to cut tissue around which it is clamped. The tissue engaging surfaces 105 may have perturbations to aid in gripping clamped tissue. The perturbations along tissue engaging surface 105 may vary in amplitude, for example, increasing towards a distal tip, in order to mitigate against the possibility of the clip 100 sliding off the clamped tissue. The tissue engaging surfaces 105 of the jaws 102 otherwise adopt a relatively linear profile, but for the perturbations, in order that, as much as possible, even compression is applied to clamped tissue when the clip 100 is in the closed position.

The jaws 102 have a distally tapering shape from the part where they are coupled to the arms 103. However, the inwardly extending portion of each of the jaws 102 serves to extend the tissue engaging surfaces of the jaws 102 in a proximal direction. As is shown in FIG. 1, there is a gap between the inwardly extending portions of the jaws 102 and the arms 103. Further, the inwardly extending portions also define a gap with the base portion 101. Although the inwardly extending portions of the jaws 102 may offer a degree of flexion when performing a clamping function or transitioning between the open and closed positions, the inwardly extending portions of the jaws 102 generally do not contact the arms, the base portion or each other. In an ideal configuration in which the clamped tissue is generally evenly clamped in between the jaws 102 when the clip 100 is in the closed position, the tissue engaging surfaces 105 are roughly parallel and spaced apart as shown in FIG. 2B. In such a position, the clip 100 has an overall shape preferably approximating a tear drop, with the base portion 101 approximating a larger rounded end of the tear drop shape.

The clip 100 is generally symmetric about a longitudinal centerline that extends through the centre of the base portion 101 and midway between the jaws 102. Depending on the particular surgical application for which a clip 100 is desired, the clip 100 may be formed to have varying dimensions. For example, the length of the clip 100, which is its largest dimension, may be around 3 millimeters to around 15 to 50 millimeters, for example, with a width of 1 to 2 millimeters to around 5 or 10 millimeters, for example, a thickness of the clip 100 may be about 1 millimeter to about 4 millimeters, for example.

The inwardly extending portions of jaws 102 may have proximal hooked portions 104 at their inward-most proximal parts, effectively providing a curved inward end intended to avoid catching or hooking clamped tissue in an area between the base portion 101 and the proximal ends of the inwardly extending portions of the jaws 102. As illustrated in FIG. 1, the inwardly extending portions of jaws 102 may taper slightly inwardly in a proximal direction until they start to curve outwardly in an outward hook shape close to the base portion 101.

The clip 100 may also be considered to have a closed end defined by the base portion 101 and an open end defined by the distal tips 106 of the jaws 102, with the jaws 102 generally defining an angle between say 0 and 45° relative to each other between the closed and open positions. Except where the clip 100 may be too large for the tissue being clamped or excessive clamping force is applied, the jaws 102 may generally not contact each other in the closed or open positions. Where excessive clamping force is applied or the clip 100 is too big for the clamped tissue, the shape memory may tend to cause the jaws 102 to contact each other towards their distal ends 106.

It is also to be observed that the jaws 102 act as the primary functional component of the clip in providing a clamping action, as required. The arms/arches 103 and base portion/ear 101 may thus act as a coupling portion that joins the opposed jaws 102. In this sense, the opposed jaws each have opposed first and second free ends (i.e. distal tips 106 and opposed proximal hook portions 104), with the coupling portion, formed by base portion 101 and arms 103, being coupled to each jaw 102 at a location intermediate the opposed free ends of each jaw 102. Thus, since the coupling portion 101/103 is formed of a shape memory alloy (at least in the base portion 101), the coupling portion causes relative movement of the jaws in response to a change in temperature of the coupling portion, depending on whether the temperature change that causes a cooling or heating activation of the shape memory of the shape memory alloy. The relative movement of the jaws 102 is primarily an increase or decrease in angular separation between the two jaws 102.

Case Study 1

Patient B aged 48 was admitted to a surgical department for a prescribed surgery to treat his chronic calculous cholecystitis. The patient had had the condition for the last 5 years, suffering several aggravations approximately 5-7 times a year when the prescribed diet was violated.

The patient was diagnosed with a gallstone disease based on his anamnesis, clinical and laboratory data and data from the ultrasound of the abdomen, which revealed a gallbladder sized 8×6×5 cm, with thickened walls up to 2.3 mm, containing a large number of stones sized up to 3 cm.

The patient has undergone a laparoscopic cholecystectomy.

During the surgery, the abdominal area was inspected and no other pathologies were found. The size of the gallbladder corresponded to the discoveries of the ultrasound, i.e. a size of 8×6×5 cm, with thickened walls and signs of chronic inflammation and the presence of multiple stones in the bladder. There were also adhesions around the neck and body of the gallbladder.

The neck and the body of the gallbladder were isolated from the adhesions with the help of a 5 mm hooked electrode. A medical clip analogous to clip 100 opened up at a 045° angle made of nitinol was introduced through a 10 mm trocar into the abdominal cavity with an endoscopic manipulator analogous to endoscopic manipulator 161. Being directly visible, the clips were then applied to the distal parts of a cystic duct and a cystic artery, followed by a similar clipping of the proximal ends of these organs. The ear was heated to over 40° C. and the cystic duct and the artery were blocked. As directly observed, reliable clamping of vessels without any signs of leakage of blood or bile was achieved.

After removal of the gallbladder from the abdominal cavity through the trocar, the shape memory effect of the clips was tested. The ear of the clip was cooled to below 10° C. and the jaws opened within 1-2 seconds. The clip was then easily removed from the cystic duct and reapplied again. This feature would be very useful for the re-application and adjustment of the clip 100 if the initial placement was not correct in the first time or requires some fine tuning for optimal results.

Further, the laparoscopic cholecystectomy was then completed following the standard procedure.

The postoperative recovery was uneventful. The patient was discharged on day 4.

Case Study 2

Patient L aged 52, was admitted to the surgical department for a prescribed surgery for the excision of varicose veins in both legs. Medical history of the condition was about 8 years. In the past 2 years the pain in the calf muscles had increased, during walking and long distance travel on foot. An annual hospitalisation for phlebothrombosis and tromboflebitis were also noted. The conservative therapy performed in the past was not effective enough. During the examination the blood flow within the deep veins of both lower extremities was not blocked.

The right-side phlebotomy (removal of veins) was carried out.

The surgery followed traditional methods. The distinctive step was the positioning of two clips analogous to clips 100 made of nitinol (nickel-titanium NiTi) onto the superficial femoral vein of the hip, in the area right before this vein intersected with the deep vein. The clip was applied to the vein with the help of the manipulator by closing the jaws as the clip's ear was heated to above 40° C.

Other vessels of small and medium-size were also clipped as the nitinol clips were placed onto the distal and proximal sections of the vessels.

The wavy surface of each of the jaws as well as notches present on the surface, helped to place the clips securely on the blood vessels. In the case of incorrect application, the clip could be removed by cooling the ear to below 10° C. with a manipulator, which would result in the clip's jaws opening and the clip could subsequently be removed. Six veins (12 clips) were clipped during the procedure. No bleeding from veins was observed. Then the operation followed a standard procedure.

The postoperative recovery was uneventful. The patient was discharged on day 2 after the surgery.

In the case studies described above, the clip 100 and manipulators 151, 161 were demonstrated to be a useful alternative to a standard clipper for stopping the bleeding e.g. Autosuture and Stortz, to mini-clips Aesculap or a manual suture. The use of clips 100 accelerates a surgery significantly, while the quality and reliability of the device is not inferior to a mechanical clipping or a manual suture.

Much of the original description of the embodiments is contained in PCT/RU2010/000735 and written in the Russian language. Much of that original text is reproduced herein in one version of an English translation. Since translations can be performed subjectively according to the skill of the translator, an alternative translation of the claims and claim language of the original Russian language document is included herein. This alternative translation describes the embodiments in the following terms:

Some embodiments relate to a method of securing hemostasis with possible consequent blood circulation restoration in elastic tubular body structures implemented by using a clip delivered to the target application point by means of a manipulator holder which mechanically holds said clip by its eye with a mechanical contact with the working surfaces of at least one Peltier thermocouple installed at the distal ends of the manipulator holder branches, said method comprising deforming the elastic tubular body structure by applying pressure developed by the closing clip branches which were preliminarily drawn apart at a temperature below the onset of the martensitic transformation in the clip eye material, wherein the pressure is produced by translating the moment of force to the clip branches via its arches from the clip eye the material of which generates reactive stresses due to the shape memory effect initiated by an increase in the eye material temperature caused by the mechanical and thermal contact of the eye material with the Peltier thermocouple surfaces switched to the heating mode, followed by discontinuation of the direct mechanical and thermal contact of the eye material with the Peltier thermocouple surfaces while retaining a compression action sufficient for securing the hemostasis at the point of application to the elastic tubular body structures produced by the working surfaces of the clip branches as the clip eye is cooled down to the body tissue temperature, and subsequent restoration of blood circulation by producing an aperture in the elastic tubular body structures due to a reduction of the pressure developed by the working surfaces of the clip branches and their partial opening as the clip eye is cooled down to below the clip eye material martensitic transformation onset temperature due to the mechanical and thermal contact of the eye material with the working surfaces of the Peltier thermocouple switched to cooling mode.

The preliminary opening of the clip branches may be achieved at a temperature of below 20° C. The shape memory effect in the clip eye material may occur at above 35° C. during 0.1-10 s. Complete or partial blood circulation restoration may be achieved by producing an aperture in the elastic tubular body structures. Partial opening of the clip branches for blood circulation restoration may be achieved at a temperature of below 20° C. during 0.1-10 s.

Some embodiments relate to a medical clip made from a biologically inert material compatible with living tissues comprising an eye the ends of which are connected with two branches via two arches, wherein the proximal ends of the branches are located in the space between the clip arches, and at least the eye of said medical clip is made from a shape memory effect material.

The eye of said medical clip may be made from medical titanium nickelide. The eye of said medical clip may have a variety of shapes, for example, semicircular, ellipsoidal, U-shaped or zigzag shaped one. The maximum allowed branch opening angle and the average compression force of the medical clip may be determined by the shape and size of the medical clip eye. The proximal ends of the branches may be located in the space between the clip arches and the clip eye. Both branches of said medical clip may have equal or different lengths ranging from 2 to 50 mm. Said branches may have variable or constant thickness across their length.

All or part of the working surfaces of the branches may have even and smooth, or wave-shaped and smooth, or even and rough, or wave-shaped and rough profile. All or part of the working surfaces of said medical clip branches may have straight or skewed notches. All or part of the working surfaces of said medical clip branches have straight or skewed ridges. The length of the medical clip arches may not exceed the length of the respective clip branches, and the thickness and width of said medical clip arches may be determined by the thickness and width of the eye. The compression force distribution profile across the length of said medical clip branches is determined by the variable size of the clip arches and the point of clip arch connection to said branches.

Some embodiments relate to a surgical manipulator holder comprising a top and a bottom elastic branches located one along the other with a gap between them and connected at their proximal ends, wherein the surface of at least the distal parts of said top and bottom elastic branches is made from a biologically inert material, the lateral sizes of said top and bottom elastic branches are smaller than their longitudinal sizes, and the distal end of at least one branch has Peltier thermocouples connected via electrically conducting and insulated wires running along said branches to a power unit having at least a three-way Peltier thermocouple mode switching box.

The distal ends of said top and bottom elastic branches may be attached with each other by means of screws, welding, soldering or gluing. The lateral sizes of said top and bottom elastic branches may vary across the branch length. The Peltier thermocouples may be attached by means of soldering or screws.

The power unit may be a direct or alternating current source. The Peltier thermocouple mode switching box may be in the form of a forced heating button and a forced cooling button provided in the middle parts of one of said branches, opposite which a forced heating microswitch and a forced cooling microswitch are provided on the other branch and are connected to said power unit installed in the distal part of said top branch. The Peltier thermocouple mode switching box may be in the form of a foot switching pedal having a power unit and connected to said surgical manipulator holder via an electric jack provided on the distal ends of said top and bottom branches.

The middle part of said surgical manipulator holder may have a branch clamp comprising a slider, a stop key rigidly connected with said top branch and freely passing through an opening in said bottom branch, slider guides and a guiding groove in said top branch in which said slider guides are provided and rigidly fixed to its bottom part. The surgical manipulator holder may have visible light and/or audible alarms.

Some embodiments relate to an endoscopic manipulator holder comprising two elastic branches at least one of which is movable, wherein said elastic branches are provided at the distal end of said manipulator holder, and their surfaces are made from a biologically inert material, the free end of at least one branch has Peltier thermocouples connected via electrically conducting wires running inside a hollow elastic pin having a rotation mechanism installed between the proximal end of said pin and a handpiece, to a power unit having at least a three-way Peltier thermocouple mode switching box, the other ends of said elastic branches cross in the first connecting unit provided at the distal end of said hollow elastic pin and linked with a traction rod running through said hollow elastic pin and movably connected with the rear handle of said handpiece which is movably connected with the front handle of said handpiece via the second connecting unit, and the rear handle of said handpiece has a connection point for a rack gear running via a through opening in the front handle of said handpiece the other end of which has a pressure plate.

The rotation mechanism may be connected with the top part of said front handle. said front handle has a finger opening. The movable connection between said traction rod and said rear handle of said handpiece may be achieved by means of a fastening socket provided in the top part of said rear handle above the second connecting unit in which the head of said traction rod is secured. The three-way Peltier thermocouple mode switching box can be in the form of forced heating and cooling microswitches provided on said front or rear handles and connected to a power unit provided in said handpiece. The Peltier thermocouple mode switching box can alternatively be in the form of a foot switching pedal having a power unit and connected to said endoscopic manipulator holder via an electric jack provided on said handpiece. The endoscopic manipulator holder can have visible light and/or audible alarms.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A clip comprising:
a base portion;
first and second opposed arms coupled to the base portion; and
first and second opposed jaws coupled to the first and second arms, respectively, the first and second opposed jaws each having an inwardly extending portion that has a free end that extends towards the base portion when the jaws are in an open position;
wherein each jaw comprises an inner tissue engaging surface, and the engaging surfaces of the jaws are generally parallel and opposed to one another when the jaws are in a closed position;
wherein at least the base portion is formed of a shape memory alloy tending to force the first and second arms toward each other and toward the closed position when a temperature of the base portion meets or exceeds a transformation temperature of the base portion;
wherein the first and second jaws each have free end portions extending away from the base portion, the free end portions being distal of the inwardly extending portions;
wherein the free end of each inwardly extending portion curves toward the respective first and second arms in a proximal direction; and
wherein the first and second jaws are separable to adopt the open position in which the jaws are acutely angled relative to each other.

2. The clip of claim 1, wherein an outer surface of the clip along the base portion and the first and second opposed arms is generally smooth.

3. The clip of claim 1, wherein the clip is formed of biologically inert materials.

4. The clip of claim 1, wherein the end portions extending away from the base portion have rounded tips.

5. The clip of claim 1, wherein in the open position, the jaws do not contact each other.

6. The clip of claim 1, wherein when a shape memory of the base portion is activated by heating the base portion, the base portion tends to force the first and second jaws toward the closed position.

7. The clip of claim 6, wherein, in the closed position, the inwardly extending portions do not contact each other.

8. The clip of claim 1, wherein at least the base portion is formed of nitinol.

9. The clip of claim 1, wherein the base portion, the arms and the jaws comprise the same material.

10. The clip of claim 1, wherein the base portion, the arms and the jaws are integrally formed.

11. The clip of claim 1, wherein the first and second jaws have perturbations formed along at least part of the inner engaging surfaces.

12. The clip of claim 1, wherein the base portion defines at least one land for contact with a temperature modification element.

13. The clip of claim 12, wherein the at least one land comprises opposed lands and the clip can be held for surgical application by gripping the opposed lands.

14. A cartridge comprising a plurality of the clips of claim 1.

15. The cartridge of claim 14, wherein the plurality of clips are held in the cartridge in an open position.

16. A kit comprising at least one clip, wherein the at least one clip comprises the clip of claim 1, the kit further comprising a clip manipulator, the clip manipulator comprising:
- at least one arm to hold one of the at least one clip, and
- at least one thermoelectric transducer to impart a temperature change to the base portion of the at least one clip sufficient to cause the temperature of the base portion to meet or exceed the transformation temperature.

17. The kit of claim 16, wherein the at least one arm comprises two arms.

18. The kit of claim 16, wherein the at least one thermoelectric transducer is coupled to a distal end of the at least one arm or each of the at least one arm.

19. The kit of claim 16, wherein the at least one thermoelectric transducer is operable to cool or heat the base portion.

20. The kit of claim 16, wherein the at least one thermoelectric transducer comprises at least one Peltier element.

21. The kit of claim 16, wherein the at least one arm of the clip manipulator comprises a distal pair of opposed jaws arranged with one thermoelectric transducer on each jaw, wherein the opposed jaws of the clip manipulator are useable to simultaneously grip the base portion of the clip and impart the temperature change thereto.

* * * * *

UNITED STATES PATENT AND TRADEMARK OFFICE
CERTIFICATE OF CORRECTION

| | | |
|---|---|---|
| PATENT NO. | : 10,064,623 B2 | Page 1 of 1 |
| APPLICATION NO. | : 13/991831 | |
| DATED | : September 4, 2018 | |
| INVENTOR(S) | : Mikhail Soutorine et al. | |

It is certified that error appears in the above-identified patent and that said Letters Patent is hereby corrected as shown below:

On the Title Page

Item (75) Inventors, delete "Artem Nikolaevich Chemov-Haraev" and insert in its place --Artem Nikolaevich Chernov-Haraev--

Item (75) Inventors, delete "Sergei Dimitrievich Prokoshin" and insert in its place --Sergei Dmitrievich Prokoshkin--

Item (75) Inventors, delete "Irina Yurievna Khmelvskaya" and insert in its place --Irina Yurievna Khmelevskaya--

Item (73) Assignee, delete "The Federal State Autonomous Educational Institution of the Higher Professional Education 'National University of Science and Technology'" and insert in its place --The Federal State Autonomous Educational Institution of the Higher Professional Education "National University of Science and Technology 'MISIS'"--

Signed and Sealed this
Sixteenth Day of July, 2019

Andrei Iancu
*Director of the United States Patent and Trademark Office*